United States Patent [19]
Tonomura et al.

[11] Patent Number: 5,693,258
[45] Date of Patent: *Dec. 2, 1997

[54] METHOD FOR IMPROVING FOAMING PROPERTIES AND FOAMING COMPOSITION

[75] Inventors: Manabu Tonomura, Tochigi; Tsuyoshi Ohtomo, Saitama, both of Japan

[73] Assignee: Kao Corporation, Tokyo, Japan

[*] Notice: The term of this patent shall not extend beyond the expiration date of Pat. No. 5,554,315.

[21] Appl. No.: 219,937

[22] Filed: Mar. 30, 1994

[30] Foreign Application Priority Data

Mar. 30, 1993 [JP] Japan .................. 5-072143

[51] Int. Cl.$^6$ .............. B01J 13/00; B01F 17/34; B01F 17/42
[52] U.S. Cl. .......... 252/356; 252/307; 252/351; 510/119; 510/130; 510/135; 510/235; 510/421
[58] Field of Search ................. 252/307, 351, 252/356; 510/135, 235, 421, 130, 119, 505

[56] References Cited

U.S. PATENT DOCUMENTS

| | | | |
|---|---|---|---|
| 3,164,476 | 1/1965 | Dalby et al. | 252/356 |
| 4,451,390 | 5/1984 | Flannigan | 252/321 |
| 4,732,753 | 3/1988 | Fuller | 424/85 |
| 4,780,249 | 10/1988 | Pittz et al. | 252/DIG. 14 |
| 5,290,479 | 3/1994 | Clark | 252/351 |
| 5,444,041 | 8/1995 | Owen et al. | 514/2 |
| 5,554,315 | 9/1996 | Tonomura et al. | 510/535 |

FOREIGN PATENT DOCUMENTS

| | | |
|---|---|---|
| 0 115 888 | 8/1984 | European Pat. Off. |
| 0 408 965 | 1/1991 | European Pat. Off. |
| 39 10 652 | 10/1990 | Germany |

OTHER PUBLICATIONS

Rosen, *Surfactants and interfacial phenomenon*, (John Wiley & Son, Inc., NY, NY 1978) pp. 210–219.
PTO 95-5701, Aug. 1995, Translation of J61–210023.
Database WPI, Derwent Publications Ltd., AN 77-29986Y, JP-A-52 034 942, Mar. 17, 1977.
Database WPI, Derwent Publications Ltd., AN 86-287940, JP-A-61 210 023, Sep. 18, 1986.
Derwent Abstract, AN-90-306189/41, (1990), Week (9041).

*Primary Examiner*—Richard D. Lovering
*Assistant Examiner*—Daniel S. Metzmaier
*Attorney, Agent, or Firm*—Oblon, Spivak, McClelland, Maier & Neustadt, P.C.

[57] ABSTRACT

A method for improving the foaming property of a nonionic surfactant having a straight-chain alkyl group containing from 10 to 16 carbon atoms, and an HLB value of about 13.5 or more is disclosed, which comprises adding (b) a fatty acid monoglyceride represented by formula (I):

$$R^1\text{—CO—OCH}_2\text{CH(OH)CH}_2\text{OH} \qquad (I)$$

wherein $R^1$ represents a straight-chain alkyl group having from 9 to 15 carbon atoms, to (a) the nonionic surfactant in a (b)/(a) weight ratio of from 2/8 to 6/5. A low-irritating foaming composition is also disclosed, which comprises (a) a nonionic surfactant having a straight-chain alkyl group containing from 10 to 16 carbon atoms as a hydrophobic group, and an HLB value of about 13.5 or more and (b) a fatty acid monoglyceride represented by formula (I):

$$R^1\text{—CO—OCH}_2\text{CH(OH)CH}_2\text{OH} \qquad (I)$$

wherein $R^1$ represents a straight chain alkyl group having from 9 to 15 carbon atoms, in a (b)/(a) weight ratio of from 2/8 to 6/5.

6 Claims, No Drawings

METHOD FOR IMPROVING FOAMING PROPERTIES AND FOAMING COMPOSITION

FIELD OF THE INVENTION

This invention relates to a method for improving the foaming property of a nonionic surfactant and a foaming composition comprising a nonionic surfactant. More particularly, it relates to a method for improving the foaming property of a specific nonionic surfactant having particularly low irritating properties and a low-irritating foaming composition comprising the specific nonionic surfactant and containing substantially no anionic surfactant which causes stimulation adversely affecting the skin or mucosa (i.e., irritation).

BACKGROUND OF THE INVENTION

Toiletry products, such as facial cleansers, shampoos, toothpaste, and some types of bath additives, conventionally contain anionic surfactants having an excellent foaming property as a foaming component. However, because anionic surfactants irritate the skin, less irritating foaming components have been demanded.

On the other hand, nonionic surfactants are generally less irritating and highly safe and therefore widely used in skin or hair care products such as detergents, products which come into contact with the sensitive parts including the mucosa, such as dish washing detergents, bath additives and medicines, and cosmetics which are desired to remain on the skin for an extended period of time, such as creams, emulsions and lotions. Additionally, they are preferred in detergents for infants and those who have a sensitive skin.

However, nonionic surfactants are less foamable, which is disadvantageous for use in detergents. Although foaming does not always agree with the basic performance, such as detergency, users are accustomed to foaming detergents and dislike foamless ones. Therefore, nonionic surfactants are rarely used alone in detergents and often combined with amine oxide type surfactants or anionic surfactants for obtaining better foaming. Nevertheless, the compounding ratio of these surfactants must be minimized because of their high irritation to the skin, resulting in a failure of providing sufficient foam while retaining low irritation.

In order to solve the above-mentioned problem, several methods for imparting the foaming property to nonionic surfactants have been proposed to date.

Examples of such techniques include a composition containing an alkyl glucoside nonionic surfactant which, while irritating, foams by itself with a specific manipulation of formulation (as disclosed in JP-A-2-32197, the term "JP-A" as used herein means an "unexamined published Japanese patent application"), a composition containing a sucrose fatty acid ester with a specific manipulation of formulation (as disclosed in JP-A-52-34941), a composition comprising a combination of a nonionic surfactant which does not foam by itself and an anionic surfactant thereby exhibiting foamability (as disclosed in JP-A-3-151035 or West German Patent 3237534), and a composition comprising a nonionic surfactant, endowed with the foaming property by addition of a specific polyethyleneimine polymer (as disclosed in JP-A-4-41596).

However, these systems still fail to exhibit a sufficient foaming property or sufficiently reduced irritation. It has thus been difficult to satisfy both the requirements of satisfactory foaming and low irritation.

SUMMARY OF THE INVENTION

Objects of the present invention are to provide a method for improving the foaming property of a nonionic surfactant which is less irritating to the skin or mucosa and to provide a composition which exhibits a satisfactory foaming property while retaining low irritation.

The present inventors have conducted extensive investigations to obtain a composition comprising a low-irritating nonionic surfactant, which lathers well without impairing the low-irritating properties of the nonionic surfactant. As a result, it has now been found that a nonionic surfactant having a relatively high HLB value which is low-irritating but hardly foams alone can be endowed with an excellent foaming property by adding, in a specific weight ratio, a fatty acid monoglyceride which is a nonionic surfactant of low HLB. The present invention has been completed based on this finding.

The present invention relates to a method for improving the foaming property of a nonionic surfactant having a straight-chain alkyl group containing from 10 to 16 carbon atoms, and an HLB value of about 13.5 or more, which comprises adding (b) a fatty acid monoglyceride represented by formula (I)

$$R^1\text{—CO—OCH}_2\text{CH(OH)CH}_2\text{OH} \quad (I)$$

wherein $R^1$ represents a straight-chain alkyl group having from 9 to 15 carbon atoms, to (a) the nonionic surfactant in a (b)/(a) weight ratio of from 2/8 to 6/5.

The present invention further relates to a low-irritating foaming composition comprising:

(a) a nonionic surfactant having a straight-chain alkyl group containing from 10 to 16 carbon atoms, and an HLB value of about 13.5 or more and (b) a fatty acid monoglyceride represented by formula (I):

$$R^1\text{—CO—OCH}_2\text{CH(OH)CH}_2\text{OH} \quad (I)$$

wherein $R^1$ represents a straight chain alkyl group having from 9 to 15 carbon atoms, in a (b)/(a) weight ratio of from 2/8 to 6/5.

DETAILED DESCRIPTION OF THE INVENTION

The nonionic surfactant to be used as component (a) has a relatively high HLB value and a relatively large molecular weight among general nonionic surfactants. Component (a) is of high utility because of its especially low irritation among general low-irritating nonionic surfactants, but is seriously inferior in the foaming property.

The present invention makes it possible to impart an excellent foaming property to such a specific nonionic surfactant as has low irritation and to provide a foaming composition excellent in both low irritation and foaming property.

The foaming property as noted above can be evaluated by the following foaming test.

A hundred milliliters of a 2 % surfactant aqueous solution containing 1% by weight of purified lanoline and 1% by weight of sodium chloride are heated to 40° C. and placed in a measuring cylinder having an inner diameter of 4 cm and equipped with a cap. The cylinder with its opening closed with the cap is vertically shaken 20 times with a 10 cm amplitude for 10 seconds. After allowing the cylinder to stand for 1 minute, the volume of the foam is measured to evaluate the foaming property of the surfactant. Shaking of the measuring cylinder is carried out by means of a shaker "TAIYO RECIPRO SHAKER SR-II" manufactured by Taiyo Kagaku Kogyo Co., Ltd.

When used alone, component (a) has such a low foaming property as having a foam volume of less than 50 ml. In a hand washing test, it also scarcely foams. The fatty acid monoglyceride to be used as component (b) is also a hardly foamable surfactant. According to the present invention, an excellent foaming property is attained by combining of these two non-foamable components.

The terminology "HLB value" as used herein means a value obtained by the Griffin's method (see W. C. Griffin, *Surface Active Agents*, Atlas Powder Co.) and is represented by the following equation:

$$HLB=(E+P)/5$$

wherein E is the number of % by weight of polyoxyethylene in a molecule and P is the number of % by weight of polyol in a molecule.

In cases where the above equation does not apply, an HLB value is calculated according to the following equation using a cloud number A:

$$HLB = \text{cloud number } A \times 0.89 + 1.11$$

wherein the cloud number A is the number of the milliliter of a 2% phenol aqueous solution added to a solution of 0.5 g of a sample surfactant (anhydrous) in 5 ml of 98% ethyl alcohol kept at 25° C. while stirring until the solution gets white turbid.

The nonionic surfactant to be used as component (a) has a straight-chain alkyl group having from 10 to 16 carbon atoms in the hydrophobic moiety thereof. Nonionic surfactants whose hydrophobic moiety has a carbon atom number outside this range hardly foam even when combined with component (b). The terminology "straight-chain alkyl group" as used herein means a straight-chain alkyl group or a branched chain alkyl group in which the ratio of the molecular weight of a branch to that of the main chain (i.e., branching ratio) is not more than about 10% by weight, such as a methyl-branched alkyl group. Accordingly, those having an alkyl group having a high branching ratio even with the carbon atom number falling within the range of from 10 to 16, such as a polyoxyethylene adduct of Guerbet alcohol, do not substantially develop the foamability even in the method of the present invention.

The nonionic surfactant to be used as component (a) also has a polyoxyethylene chain or a polyoxyethylene/polyoxypropylene random or block copolymer chain in the hydrophilic moiety thereof. The polyoxyethylene chain or polyoxyethylene/polyoxypropylene random or block copolymer chain preferably has an average degree of polymerization (average addition mole number) of from 10 to 100.

Preferred examples of component (a) include:

(i) polyoxyalkylene alkyl ethers having from 10 to 16 carbon atoms in the alkyl moiety thereof, such as "Emulgen 123P" (polyoxyethylene lauryl ether, produced by Kao Corp., average addition mole number of polyoxyethylene: 23) and "Emalex 730" (produced by Nippon Emulsion Co., Ltd., average mole number of added polyoxyethylene: 30);

(ii) polyoxyalkylene monofatty acid esters having from 10 to 16 carbon atoms in the alkyl moiety of the fatty acid residue thereof, such as "Emanone 1112" (polyethylene glycol monolaurate, produced by Kao Corp., average addition mole number of polyoxyethylene: 12);

(iii) polyoxyalkylene sorbitan monofatty acid esters having from 10 to 16 carbon atoms in the alkyl moiety of the fatty acid residue thereof, such as "RHEODOL TWL-120" (polyoxyethylene sorbitan monolaurate, produced by Kao Corp., average addition mole number of polyoxyethylene: 20); and (iv) polyoxyalkylene glycerol monofatty acid esters having from 10 to 16 carbon atoms in the alkyl moiety of the fatty acid residue thereof (e.g., those having 12 carbon atoms in the alkyl moiety thereof and a polyoxyethylene of an average addition mole number of 20 as the polyoxyalkylene chain).

The terminology "polyoxyalkylene" as used herein includes polyoxyethylene and oxyethylene/oxypropylene random or block copolymers. The alkyl group having from 10 to 16 carbon atoms includes a capryl group, a lauryl group, a myristyl group, and a palmityl group, with a capryl group and a lauryl group being preferred from the standpoint of foam volume obtained.

Component (a) preferably has an average molecular weight of 600 or more and less than 5,000. This molecular weight range is two times or more of that of general anionic surfactants. In view of low irritation, a surfactant of a higher molecular weight is preferred since the surfactant becomes less penetrable into the skin as its molecular weight increases. However, the surfactant generally becomes less foamable as its molecular weight increases. According to the present invention, the foaming property of the nonionic surfactant, which is excellent in low irritating properties but inferior in the foaming property as discussed above, can be improved without impairing .the advantage of low irritation.

The average molecular weight as referred herein means the weight average molecular weight and it can be measured in a usual manner, such as by calculating a weight ratio of the alkyl carbon to the polyoxyethylene chain carbon obtained by $C^{13}$-NMR analysis.

Examples of the fatty acid monoglyceride to be used as component (b) include glycerol monocaprate, glycerol monolaurate, glycerol monomyristate and glycerol monopalmitate. Among them, glycerol monocaprate and glycerol monolaurate are preferred because they are highly capable of increasing the foam volume. Further, the foam produced by using glycerol monolaurate has a creamy and natural touch as with conventional soaps and meets the public taste.

As component (b) of the present invention, commercially available fatty acid monoglyceride may be used. However, since the commercially available fatty acid monoglycerides generally contain diglycerides and triglycerides, it is desirable to use the one containing the fatty acid monoglyceride in an amount of at least 80% by weight, preferably at least 90% by weight.

Components (a) and (b) are preferably blended at an (b)/(a) weight ratio of from 2/8 to 6/5 for attaining a sufficient effect of improving foaming property and for obtaining satisfactory foam quality. Taking oil-resistance and salt-resistance of foam into consideration, the (b)/(a) weight ratio is more preferably from 2/8 to 5/5, and further preferably from 3/7 to 4/6.

The method for the addition of component (b) to component (a) is not particularly restricted. For example, compound (b) is added to component (a) as such, or to a composition containing component (a) either during preparation of the composition or at the use thereof, followed by mixing with stirring. Similarly, the method for preparing the composition of the present invention is not limited, and the composition is prepared by mixing components (a) and (b) in a known manner.

If desired, the composition of the present invention may contain, in addition to components (a) and (b), commonly employed components of low irritation. This being the case, while the proportions of components (a) and (b) in the composition are not particularly limited, an aqueous composition, for example, preferably contains components (a) and (b) in a total amount of 2% by weight or more.

The composition of the present invention can be formulated into various forms, such as liquid, powder or solid, by known methods.

In order to obtain foam, the composition of the present invention must be used under an aqueous condition. Since the aqueous condition is required at least at the time of use, the composition may have a form that is to be diluted with water on use, such as solid soap.

The terminology "aqueous condition" as used herein typically means a homogeneous system comprising water as a solvent. Also included under the terminology is a system in which a water-containing liquid phase forms a continuous phase, such as a system containing an alcohol hereinafter described or a disperse system containing insoluble powders.

If desired, the composition of the present invention may further contain optional components usually added to toiletry products such as facial cleansers, shampoos, toothpaste, and bath additives, as long as the low irritation and the excellent foaming property are not impaired. For example, other known surfactants may be added to the composition. In this case, however, the blending ratio of the other surfactants should be minimized. In particular, anionic surfactants or amine oxide compounds tend to cause irritation when blended in a ratio of 1% by weight or more and decisively increases irritation in a ratio of 3% by weight or more. Further, the amount of oils to be added should also be minimized so as not to impair the foaming property.

If desired, the composition according to the present invention may further contain alcohols, water-soluble high polymers, and small proportions of stabilizers or pH adjusting agents, such as inorganic salts and amino salts. Suitable alcohols include monohydric alcohols (e.g., ethanol), and polyhydric alcohols (e.g., glycerin) and polyethylene glycol. Suitable water-soluble high polymers include natural polysaccharides (e.g., carrageenan), semisynthetic polysaccharides (e.g., hydroxyethyl cellulose), proteins (e.g., collagen), and synthetic polymers (e.g., peptides and polyacrylic acids).

These components generally tend to improve foam stability without impairing the foaming property of the surfactant, thus preferred.

While low-irritant high-molecular weight nonionic surfactants have been regarded as unsatisfactory because of their low foaming properties, the present invention makes it possible to impart a satisfactory foaming property to such nonionic surfactants without impairing their merits of low irritation. Accordingly, the present invention provides various preparations with an improved foaming property and low irritation properties, such as detergents for those having a sensitive skin, facial cleansers or shampoos which may enter the eyes during use, and preparations which will contact the skin or mucosa, such as toothpaste, anus cleaning agents, and bath additives.

The present invention will now be illustrated in greater detail with reference to Test Examples and Examples, but the present invention should not be construed as being limited thereto. All the percents are by weight except where noted.

TEST EXAMPLE 1

A composition weighing 100 g was prepared by mixing 20% of the nonionic surfactant shown in Table 1 below, 10% of glycerol monolaurate ("Sunsoft 750", produced by Taiyo Kagaku Co., Ltd.), and a balance of ion-exchanged water. A 10 g aliquot of the composition was mixed with 1 g of purified lanoline, 1 g of sodium chloride, and water to make 100 ml. The mixture was heated to 40° C. and put into a measuring cylinder having an inner diameter of 4 cm and equipped with a cap. The cylinder was vertically shaken 20 times with a 10 cm amplitude for 10 seconds by means of a shaker "TAIYO RECIPRO SHAKER SR-II" manufactured by Taiyo Kagaku Kogyo Co., Ltd. After allowing the cylinder to stand for 1 minute, the volume of the foam (lather) was measured. The results obtained are shown in Table 1.

For comparison, a composition prepared from 2 g of the same nonionic surfactant, 1 g of purified lanoline, 1 g of sodium chloride, and water in an amount to make 100 ml (the same formulation as above, except for containing no glycerol monolaurate) was tested in the same manner as described above. The results obtained are shown in the parentheses in Table 1. Among the combinations shown in Table 1, (2) to (5) are according to the present invention.

TABLE 1

| | Nonionic Surfactant* | | | | |
|---|---|---|---|---|---|
| Type | Alkyl Group | EO Chain Polymer- ization Degree | HLB Value | Average Molecular Weight | Volume of Foam (ml) |
| (1) Polyoxyethy- lene alkyl ether | $C_{12}$ | 4 | 9.6 | 380 | 45 (35)** |
| (2) Polyoxyethy- lene fatty acid ester | $C_{12}$ | 12 | 13.7 | 740 | 70 (38) |
| (3) Polyoxyethy- lene alkyl ether | $C_{16}$ | 20 | 14.2 | 1,100 | 70 (25) |
| (4) Polyoxyethy- lene sorbitan fatty acid ester | $C_{12}$ | 20 | 16.7 | 1,200 | 120 (25) |
| (5) Polyoxyethy- lene alkyl ether | $C_{12}$ | 23 | 16.9 | 1,200 | 230 (30) |
| (6) Polyoxyethy- lene fatty acid ester | $C_{18}$ | 15 | 13.4 | 1,000 | 30 (15) |
| (7) Polyoxyethy- lene alkyl ether | $C_{18}$ | 20 | 14.9 | 1,200 | 45 (20) |
| (8) Polyoxyethy- lene fatty acid ester | $C_{18}$ | 140 | 19.1 | 6,500 | 45 (20) |

Note:
*All the surfactants except (5) are products of Kao Corp. The surfactant (5) is a product of Nippon Emulsion Co., Ltd.
**Values in the parentheses are foam volumes when the fatty acid monoglyceride was not used in combination.

As is apparent from the results in Table 1, a combination of a nonionic surfactant and a fatty acid monoglyceride according to the present invention exhibits a markedly improved foaming property as compared with a combination which does not satisfy the requirements specified in the present invention.

TEST EXAMPLE 2

A composition comprising 2 g of the nonionic surfactant shown in Table 2 below, 1 g of purified lanoline, 1 g of sodium chloride, and 96 g of ion-exchanged water was heated to 40° C. and tested in the same manner as in Test Example 1. After measuring the foam volume, the composition was returned to a beaker, and 0.8 g of the fatty acid glyceride shown in Table 2 was added thereto. The mixture was again heated to 40° C. and tested in the same manner. The foaming properties were evaluated according to the following criterion. The results of evaluation are shown in Table 2.

Criterion of Evaluation:
  A: The foam volume was 50 ml or more.
  B: The foam volume was less than 50 ml.

The compositions providing a foam volume of 50 ml or more in the above foaming test were recognized to lather well in a hand washing test.

TABLE 2

| Type | Nonionic Surfactant[1] | | | | Fatty Acid Monoglyceride[2] | | | | | |
|---|---|---|---|---|---|---|---|---|---|---|
| | Alkyl Group | EO Chain Polymerization Degree | HLB Value | Average Molecular Weight | $C_{10}$ | $C_{12}$ | $C_{14}$ | $C_{16}$ | $C_{18}$ | None |
| (1) Polyoxyethylene alkyl ether | $C_{12}$ | 4 | 9.6 | 380 | B | B | B | B | B | B |
| (2) Polyoxyethylene fatty acid ester | $C_{12}$ | 12 | 13.7 | 740 | A | A | A | A | B | B |
| (3) Polyoxyethylene alkyl ether | $C_{16}$ | 20 | 14.2 | 1,100 | A | A | A | A | B | B |
| (4) Polyoxyethylene sorbitan fatty acid ester | $C_{12}$ | 20 | 16.7 | 1,200 | A | A | A | A | B | B |
| (5) Polyoxyethylene alkyl ether | $C_{12}$ | 23 | 16.9 | 1,200 | A | A | A | A | B | B |
| (6) Polyoxyethylene fatty acid ester | $C_{18}$ | 15 | 13.4 | 1,000 | B | B | B | B | B | B |
| (7) Polyoxyethylene alkyl ether | $C_{18}$ | 20 | 14.9 | 1,200 | B | B | B | B | B | B |
| (8) Polyoxyethylene fatty acid ester | $C_{18}$ | 140 | 19.1 | 6,500 | B | B | B | B | B | B |

Note:
[1] Surfactants (1) to (4) and (6) to (8) are products of Kao Corp. Surfactant (5) is a product of Nippon Emulsion Co., Ltd.
[2] $C_{10}$: glycerol monocaprate ("Sunsoft 760", produced by Taiyo Kagaku Co., Ltd.)
$C_{12}$: glycerol monolaurate (Sunsoft 750H)
$C_{14}$: glycerol monomyristate ("Sunsoft 8002", produced by Taiyo Kagaku Co., Ltd.)
$C_{16}$: glycerol monopalmitate ("Sunsoft 8001", produced by Taiyo Kagaku Co., Ltd.)
$C_{18}$: glycerol monostearate (a product of Kao Corp.)

As is apparent from the results in Table 2, addition of a fatty acid monoglyceride which satisfies the requirements specified in the present invention to a nonionic surfactant which satisfies the requirements specified in the present invention improves the foaming property of the nonionic surfactant, which does not foam when used alone, thereby providing a composition having a satisfactory level of foamability. Where either the nonionic surfactant or the fatty acid monoglyceride failed to satisfy the respective requirements, a sufficient foaming property was not obtained.

EXAMPLES 1 TO 5 AND COMPARATIVE EXAMPLES 1 TO 8

A composition shown in Table 3 below was mixed while heating to 60° C. and then allowed to cool to room temperature. Subsequently, the composition was subjected to a hand washing test by specialized panel members as follows. An adequate amount of the composition was thoroughly foamed by hands, and the foaming properties were evaluated according to the following criterion. The results obtained are shown in Table 3.

Criterion of Evaluation:
A: Continuous foam (lather) was obtained.
B: Continuous foam (lather) was not obtained.

TABLE 3*[1]

| Component | Example No. | | | | | Comparative Example No. | | | | | | | |
|---|---|---|---|---|---|---|---|---|---|---|---|---|---|
| | 1 (%) | 2 (%) | 3 (%) | 4 (%) | 5 (%) | 1 (%) | 2 (%) | 3 (%) | 4 (%) | 5 (%) | 6 (%) | 7 (%) | 8 (%) |
| Polyoxyethylene (30) lauryl ether*[2] | 40 | — | — | — | — | 40 | — | — | — | — | — | — | — |
| Polyoxyethylene (23) lauryl ether*[3] | — | 40 | 30 | — | — | — | — | 20 | 49 | 20 | — | — | — |
| Polyoxyethylene (20) sorbitan monolaurate*[4] | — | — | — | 40 | 30 | — | — | — | — | — | 50 | 49 | 20 |
| Glycerol monolaurate*[5] | 20 | — | — | 10 | 20 | — | 20 | — | — | — | — | 1 | 30 |
| Glycerol monopalmitate*[6] | — | 10 | 20 | — | — | — | — | — | 1 | 30 | — | — | — |
| Ion-exchanged water | balance | balance | balance | balance | balance | balance | balance | balance | balance | balance | balance | balance | balance |
| Foaming in Hand Washing | A | A | A | A | A | B | B | B | B | B | B | B | B |

Note:
*[1] Amounts of the components are % by weight.
*[2] Emalex 30, produced by Nippon Emulsion Co., Ltd.
*[3] Emulgen 124, produced by Kao Corp.
*[4] RHEODOL TWL=120, produced by Kao Corp.
*[5] Sunsoft 740 produced by Taiyo Kagaku Co., Ltd.
*[6] Sunsoft 8001 produced by Taiyo Kagaku Co., Ltd.

EXAMPLE 6

(Facial Cleanser)

| Components | Amount (% by weight) |
|---|---|
| (1) Polyoxyethylene glycol laurate (average addition EO mole number: 20; total molecular weight: 1,100) | 20.0 |
| (2) Glycerol monolaurate ("Sunsoft 750H" produced by Taiyo Kagaku Co., Ltd.) | 8.0 |
| (3) Monosodium citrate | 0.1 |
| (4) Propylene glycol | 4.0 |
| (5) Magnesium stearate | 0.1 |
| (6) Polyethylene glycol (molecular weight: 25,000; "Alkox E-100" produced by Meisei Kagaku Kogyo K. K.) | 0.1 |
| (7) Antiseptic (methylparaben) | appropriate amount |
| (8) Flavor | appropriate amount |
| (9) Purified water | balance |
| Total | 100 |

The facial cleanser having the above formulation showed a foaming property equal to ordinary soap-based facial cleansing products and felt light and soft to the skin. No particular irritation was perceived when used by persons having a sensitive skin.

EXAMPLE 7

(Soap)

| Components | Amount (% by weight) |
|---|---|
| (1) Polyoxyethylene (50) lauryl ether ("Emalex 750" produced by Nippon Emulsion Co., Ltd.) | 55.0 |
| (2) Glycerol monolaurate (Sunsoft 750H) | 25.0 |
| (3) Glycerol monocaprate (Sunsoft 760) | 4.0 |
| (4) Sorbitol (powder) | 1.2 |
| (5) Dipotassium glycyrrhetinate | 0.02 |
| (6) Solid paraffin | 0.05 |
| (7) Soluble starch | 15.0 |
| (8) Flavor | trace |
| (9) Purified water | balance |
| Total | 100 |

The soap having the above formulation lathered well and, after use, gave no dry feel to the skin but rather made the user feel the skin get softer.

While the invention has been described in detail and with reference to specific examples thereof, it will be apparent to one skilled in the art that various changes and modifications can be made therein without departing from the spirit and scope thereof.

What is claimed is:

1. A method for increasing the foaming property of a nonionic surfactant having a straight-chain alkyl group containing from 10 to 16 carbon atoms, a polyoxyethylene or polyoxyethylene/polyoxypropylene random or block copolymer chain, an HLB value of about 13.5 or more, and an average molecular weight of from 600 to less than 5,000, which consisting essentially of mixing (b) a fatty acid monoglyceride represented by formula (I):

$$R^1\text{—CO—OCH}_2\text{CH(OH)CH}_2\text{OH} \qquad (I)$$

wherein $R^1$ represents a straight-chain alkyl group having from 9 to 15 carbon atoms, and (a) the nonionic surfactant in a (b)/(a) weight ratio of from 2/8 to 6/5.

2. A method of claim 1, wherein said nonionic surfactant is selected from the group consisting of polyoxyalkylene alkyl ethers, polyoxyalkylene monofatty acid esters, polyoxyalkylene sorbitan monofatty acid esters, and polyoxyalkylene glycerol monofatty acid esters.

3. A method of claim 1, wherein said fatty acid monoglyceride is glycerol monocaprate, glycerol monolaurate or a mixture of glycerol monocaprate and glycerol monolaurate.

4. A low-irritating foaming composition consisting essentially of:

(a) a nonionic surfactant having a straight-chain alkyl group containing from 10 to 16 carbon atoms, a polyoxyethylene or polyoxyethylene/polyoxypropylene random or block copolymer chain, an HLB value of about 13.5 or more, and an average molecular weight of from 600 to less than 5,000, and (b) a fatty acid monoglyceride represented by formula (I):

$$R^1\text{—CO—OCH}_2\text{CH(OH)CH}_2\text{OH} \qquad (I)$$

wherein $R^1$ represents a straight chain alkyl group having from 9 to 15 carbon atoms, in a (b)/(a) weight ratio of from 2/8 to 6/5.

5. A low-irritating foaming composition of claim 4, wherein said nonionic surfactant is selected from the group consisting of polyoxyalkylene alkyl ethers, polyoxyalkylene monofatty acid esters, polyoxyalkylene sorbitan monofatty acid esters, and polyoxyalkylene glycerol monofatty acid esters.

6. A low-irritating foaming composition of claim 4, wherein said fatty acid monoglyceride is glycerol monocaprate, glycerol monolaurate or a mixture of glycerol monocaprate and glycerol monolaurate.

* * * * *